United States Patent
Diehl et al.

(10) Patent No.: US 8,360,962 B2
(45) Date of Patent: Jan. 29, 2013

(54) POSITION CONTROL OF MEDICAL APPLIANCES IN THE HUMAN BODY BY MEANS OF PHASE DIFFERENCE MEASUREMENT

(75) Inventors: Dirk Diehl, Erlangen (DE); Ralph Oppelt, Uttenreuth (DE); Johannes Reinschke, Nürnberg (DE)

(73) Assignee: Siemens Aktiengesellschaft, Munich (DE)

( * ) Notice: Subject to any disclaimer, the term of this patent is extended or adjusted under 35 U.S.C. 154(b) by 284 days.

(21) Appl. No.: 12/735,319

(22) PCT Filed: Dec. 8, 2008

(86) PCT No.: PCT/EP2008/066988
§ 371 (c)(1),
(2), (4) Date: Jul. 2, 2010

(87) PCT Pub. No.: WO2009/083409
PCT Pub. Date: Jul. 9, 2009

(65) Prior Publication Data
US 2010/0274086 A1   Oct. 28, 2010

(30) Foreign Application Priority Data
Jan. 2, 2008   (DE) .......................... 10 2008 003 005

(51) Int. Cl.
*A61B 1/00* (2006.01)
*A61B 5/05* (2006.01)
(52) U.S. Cl. ..................... 600/118; 600/117; 600/424
(58) Field of Classification Search ................ 600/118, 600/117, 107, 424
See application file for complete search history.

(56) References Cited

U.S. PATENT DOCUMENTS

| | | | |
|---|---|---|---|
| 7,032,600 B2 | 4/2006 | Fukuda et al. | |
| 7,173,507 B2 | 2/2007 | Ries | |
| 2004/0210131 A1* | 10/2004 | Fukuda et al. | ................ 600/424 |
| 2006/0122494 A1 | 6/2006 | Bouchoucha | |

FOREIGN PATENT DOCUMENTS

| | | |
|---|---|---|
| CN | 1517717 | 8/2004 |
| CN | 1589729 | 3/2005 |
| DE | 10142253 C1 | 4/2003 |
| DE | 10340925 B3 | 6/2005 |
| DE | 102006010730 A1 | 9/2006 |
| DE | 102006019415 A1 | 10/2007 |
| EP | 1440659 A2 | 7/2004 |
| WO | WO 2005104976 A1 | 11/2005 |
| WO | WO 2005120345 A2 | 12/2005 |

OTHER PUBLICATIONS

Chinese Office Action for related Chinese Patent Application No. 200880123860.7, issued on Jan. 30, 2012.

* cited by examiner

*Primary Examiner* — Rochelle-Ann J Blackman
(74) *Attorney, Agent, or Firm* — Staas & Halsey LLP

(57) ABSTRACT

A system measures a change in position of a medical appliance, such as an endoscopy capsule. A device uses this measurement in order to influence the position of the medical appliance. The medical appliance sends a signal that is received by a multiplicity of spatially separate receiving devices. The time profile of the phase differences between the received signals and a reference signal provides an indication of whether the medical appliance has moved. In the event of a movement being detected, a maneuvering device can be regulated by a regulating means in such a way that the maneuvering device generates forces and/or torques and applies them to the medical appliance to counteract the detected movement.

22 Claims, 4 Drawing Sheets

POSITION CONTROL OF MEDICAL APPLIANCES IN THE HUMAN BODY BY MEANS OF PHASE DIFFERENCE MEASUREMENT

CROSS REFERENCE TO RELATED APPLICATIONS

This application is based on and hereby claims priority to PCT Application No. PCT/EP2008/066988 filed on Dec. 8, 2008 and DE Application No. 10 2008 003 005.8 filed on Jan. 2, 2008, the contents of which are hereby incorporated by reference.

BACKGROUND

The invention relates to a system for measuring a change in position of a medical device, such as an endoscopy capsule, and to an appliance which utilizes this measurement in order to influence the position of the medical device.

Endoscopy capsules are used increasingly in medicine to diagnose or treat the inside of a patient. An endoscopy capsule can contain inter alia medical instruments for instance for biopsy or for introducing medicines into the body and/or image systems such as cameras. Furthermore, a permanent magnet can be integrated in the capsule, which affords the capsule a magnetic dipole moment, so that that it can be maneuvered at will with the aid of a magnetic coil arrangement as described in DE 103 40 925 B3 for instance.

With examinations inside the body using a medical device such as an endoscopy capsule, the position of the device is generally monitored and if necessary influenced. For instance, with an examination of the stomach, this is half filled with water and the endoscopy capsules floats on the water surface. When recording images of the inside of the stomach, the problem arises that the capsule and with it the camera are moved as a result of the water movement which cannot be avoided, so that only unclear, blurred images can be recorded. In the event that a series of images of a certain region is to be recorded, it is necessary for the capsule to be stationary.

For position determination purposes, electromagnetic measuring methods mostly use low-frequency magnetic alternating fields, which penetrate the human body in an almost uninfluenced fashion, thereby rendering an absolute position determination possible. A system of this type is described in WO 2005/120345 A2. Nevertheless, known systems on the one hand are disadvantageous in terms of a limited measuring accuracy. On the other hand, as a result of a poor signal-to-noise ratio and the necessary long integration time associated therewith, the temporal resolution is relatively minimal and the measuring value delay is comparatively great. Alternatively, phase difference measurements on high-frequency electromagnetic waves were proposed for the absolute position measurement of medical devices in the inside of the body. Account was not taken here of the fact that the wave propagation through body tissue with a different dielectric constant and conductivity results in a considerable deformation of the spherical wave front in the free space. Nevertheless, to enable an absolute position determination, complex correction methods are needed.

SUMMARY

One potential object is therefore to specify an apparatus and a method, with which a change in position of a medical device can be detected and can counteract a change of this type.

The inventors proposals assume that the absolute position of the device is not needed to control the position of a medical device inside the body and for a possible position correction but that only changes in position have to be detected in accordance with their direction and at least roughly in accordance with their size. When determining a deviation of the medical device from a target position or more generally if the medical device implements an unwanted movement, a controller can be used, which counteracts the deviation and/or the movement. It is accordingly sufficient only to implement a relative position determination.

To this end, the medical device sends high-frequency electromagnetic signals continuously or at intervals, the electromagnetic signals being received by several spatially distributed receiving devices. The temporal behavior of the phase differences between the signals received at the receiving devices and a reference signal is monitored in order to detect a movement of the medical device. The reference signal can originate here from a separate reference signal source or from one of the receiving devices. In the event that one or several of the phase differences of the receiving devices change, it is assumed that the medical device has moved, so that if necessary corresponding countermeasures can be taken to counteract the movement.

The countermeasures are triggered by a control facility as a function of the detected phase differences. The control facility controls a maneuvering apparatus for influencing the position of the medical device, with it being possible for the maneuvering apparatus to be a magnetic coil arrangement, as described in DE 103 40 925 B3.

The method is advantageous in that only one relative position measurement is implemented, such that as a result of the high signal-to-noise ratio, a rapid measurement and thus a short reaction time ensue. Deviations in the medical device from a target position are thus rapidly detected and can be correspondingly corrected at short notice before the sum of the position changes becomes too great. Furthermore, contrary to the absolute position measurements, no knowledge is advantageously needed relating to the body tissue located between the medical device and/or the transmit facility and the receiving devices (e.g. dielectric constant, conductivity).

To enable a more precise and rapid absolute position measurement, it is conceivable for the method and/or apparatus to be combined with other, e.g. low-frequency measuring methods for absolute position measurement.

BRIEF DESCRIPTION OF THE DRAWINGS

These and other objects and advantages of the present invention will become more apparent and more readily appreciated from the following description of the preferred embodiments, taken in conjunction with the accompanying drawings of which.

DETAILED DESCRIPTION OF THE PREFERRED EMBODIMENT

Figure 1:
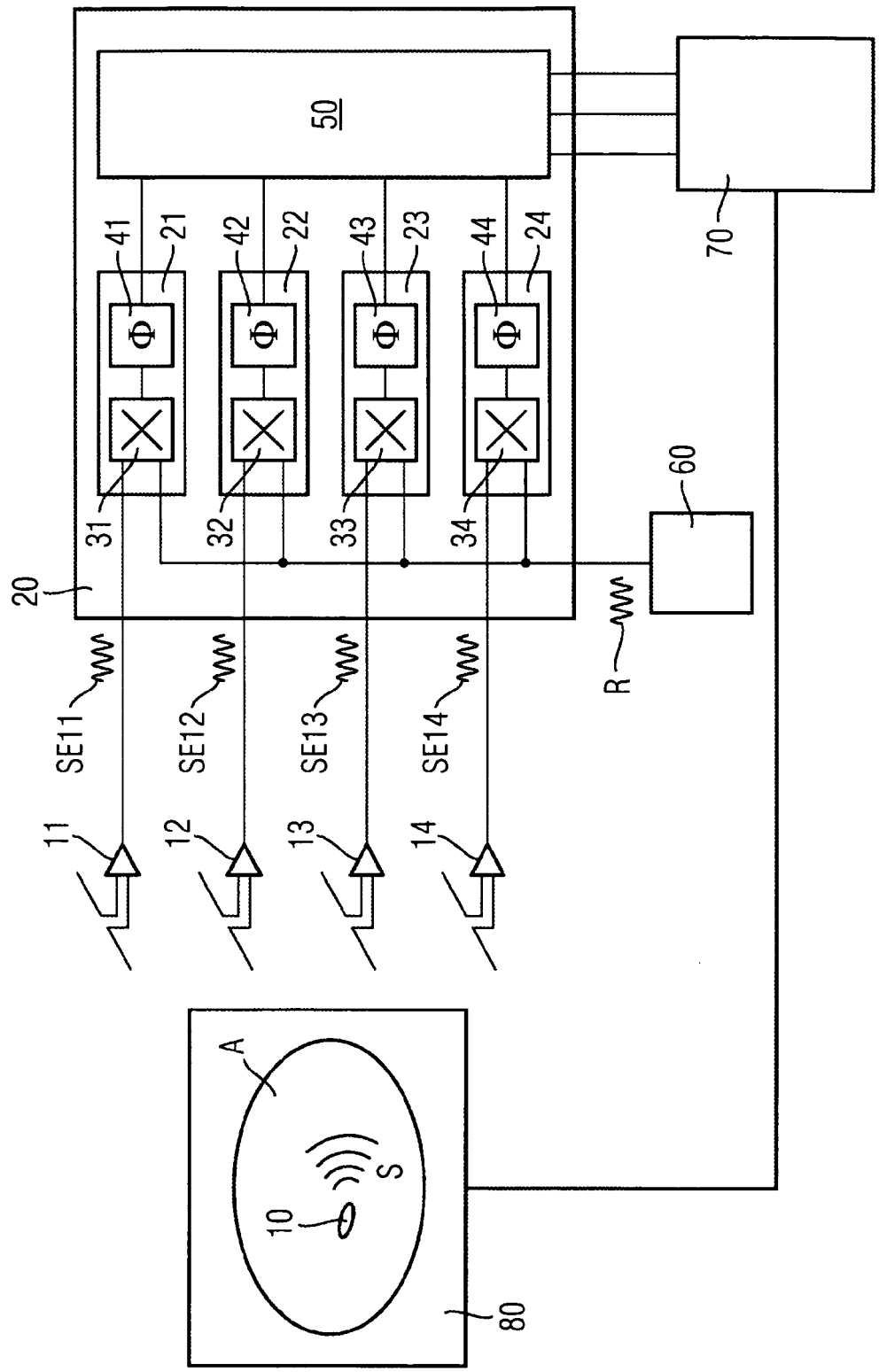
FIG. 1 shows a first exemplary embodiment of the proposed apparatus.

Reference will now be made in detail to the preferred embodiments of the present invention, examples of which are illustrated in the accompanying drawings, wherein like reference numerals refer to like elements throughout.

First Exemplary Embodiment

Figure 5:
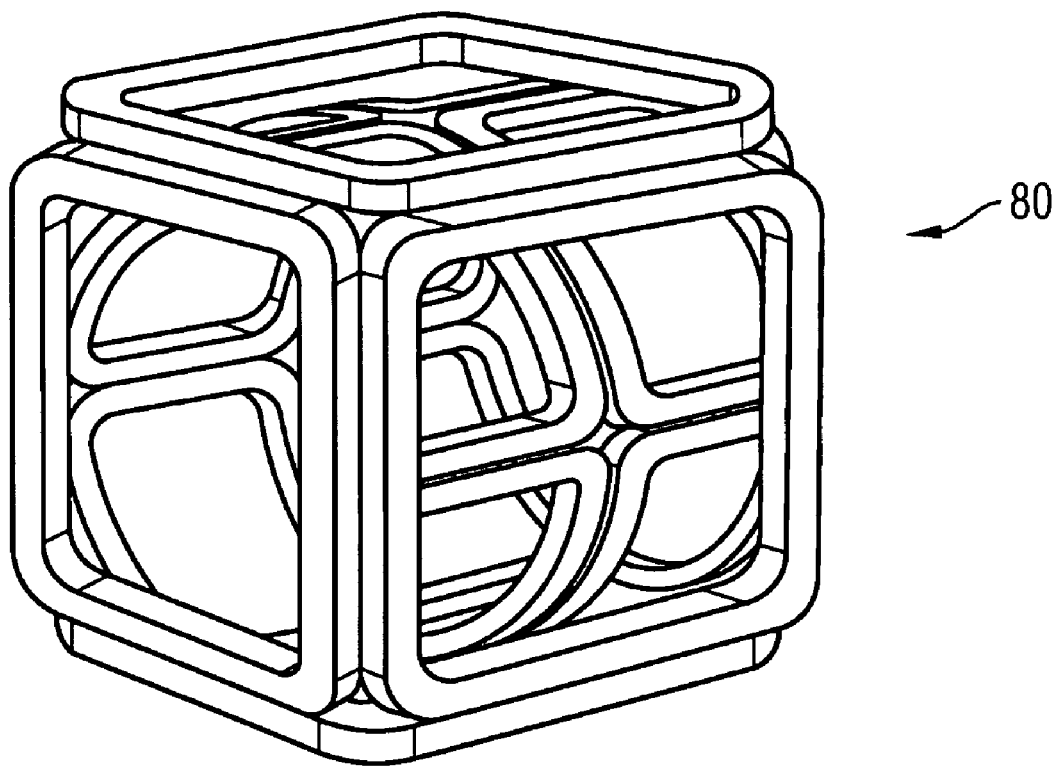
FIG. 5 shows a maneuvering apparatus.

FIG. 1 shows a first embodiment of an apparatus for controlling a position x,y,z of a medical device 10 in a workspace A. The workspace A can be a cavity in the inside of a patient, like for instance the stomach, while the medical device 10 is preferably an endoscopy capsule. The endoscopy capsule 10 is equipped with a permanent magnet and therefore has a magnetic dipole moment, so that it can be maneuvered magnetically and in a contact-free fashion with the aid of a maneuvering apparatus 80 and/or magnetic coil arrangement, as described for instance in DE 102 40 925 B3 and according to the exemplary illustration shown in FIG. 5.

Furthermore, the endoscopy capsule 10 contains a transmit facility. This sends a modulated or non-modulated signal S continuously or at intervals, for instance a high frequency signal S with a frequency of 435 MHz.

The signal S is received by one or several of four receiving devices 11-14 in the first exemplary embodiment. To this end, the receiving devices 11-14 are provided with an antenna for receiving an electrical and/or a magnetic field. Furthermore, the receiving devices 11-14 each contain a preamplifier for amplifying the received signal. The signals SE11-SE14 received and amplified with the receiving devices 11-14 are transmitted to a signal processing facility 20. The signal processing facility 20 contains several facilities 21-24, with each receive facility 11-14 being assigned a facility 21-24. The facilities 21-24 each have a first and a second signal input and a signal output, with the received signals SE11-SE14 applied in each instance at the second signal input.

Furthermore, a reference signal source 60 is provided, which generates a reference signal R. The reference signal source 60 may be a reference oscillator, the frequency of which preferably only deviates marginally from the frequency of the signal S. The reference signal R is applied at each first signal input of the facilities 21-24.

The facilities 21-24 preferably each contain a mixing device 31-34 and a phase measurer 41-44, with each mixing device 31-34 having a first and a second signal input in each instance. The first and/or second signal inputs of the facilities 21-24 correspond to the first and/or second inputs of the mixing devices 31-34. The signal outputs of the phase measurer 41-44 correspond to the signal outputs of the facilities 21-24.

The signals applied at the signal inputs of a mixing device 31-34 are mixed with one another in a known manner. The output signals of the mixing device 31-34 are each forwarded to a signal input of the phase measurer 41-44. The phase measurer 41-44 determines the phase position of the signal applied at its input, with, for instance, the signal initially being amplified such that a rectangular signal almost arises and the zero passage of the rectangular signal is then determined. The output signals of the phase measurer 41-44 then correspond in each instance to the phase deviations $d\phi_{11}, d\phi_{12}, d\phi_{13}, d\phi_{14}$ between the phases of the signals, which are applied at the first and second signal inputs of the facilities 21-24 and/or the mixing device 31-34. For instance, the signal R is applied at the first signal input of the facility 21, while the signal SE11 received at the receive facility 11 is applied at the second signal input of the facility 21. The output signal of the facility 21 then corresponds to the deviation $d\phi_{11} = \phi(SE11) - \phi(R)$ between the phase $\phi(SE11)$ of the signal SE11 and the phase $\phi(R)$ of the reference signal R. The same applies to the input and output signals of the facilities 22-24, i.e. the output signals of the facilities 21-24 correspond to the phase deviations $d\phi_{11}, d\phi_{12}, d\phi_{13}, d\phi_{14}$ between the phases $\phi(SE11)$, $\phi(SE12)$, $\phi(SE13)$, $\phi(SE14)$ of the signals SE11-SE14 received at the receiving devices 11-14 and the phase $\phi(R)$ of the reference signal R generated by the reference signal source 60.

Since the frequencies of the reference signal source 60 and the transmit facility do not generally exactly agree with the endoscopy capsule 10, the phase deviations $d\phi_{11}, d\phi_{12}, d\phi_{13}, d\phi_{14}$ do are not temporally constant but increase linearly with time. Provided that the endoscopy capsule 10 is not moved, the difference between the deviations must however be temporally constant. A difference formation apparatus 50 is therefore provided in the signal processing facility 20, into which the deviations $d\phi_{11}, d\phi_{12}, d\phi_{13}, d\phi_{14}$ are fed.

In the difference formation apparatus 50, phase differences $\Delta\phi_1, \Delta\phi_2, \Delta\phi_3$ are determined. Here any of the phase deviations $d\phi_{11}, d\phi_{12}, d\phi_{13}, d\phi_{14}$ is determined as a reference value $d\phi_{ref}$, for instance $d\phi_{ref} = d\phi_{11}$, and the difference between the remaining phase deviations $d\phi_{12}, d\phi_{13}, d\phi_{14}$ and the reference value $d\phi_{ref}$ is formed, i.e. $\Delta\phi_1 = d\phi_{12} - d\phi_{11}$, $\Delta\phi_2 = d\phi_{13} - d\phi_{11}$ and $\Delta\phi_3 = d\phi_{14} - d\phi_{11}$. The selection of one of the deviations as a reference value $d\phi_{ref}$ can take place randomly or for instance as a function of the sum of the deviations $d\phi_{11}, d\phi_{12}, d\phi_{13}, d\phi_{14}$.

The phase differences $\Delta\phi_1, \Delta\phi_2, \Delta\phi_3$ are determined temporally continuously or at intervals.

The phase differences $\Delta\phi_1, \Delta\phi_2, \Delta\phi_3$ are fed to a control facility 70. The control facility 70 is connected to a maneuvering apparatus 80 for influencing the position x, y, z of the endoscopy capsule 10 and uses the phase differences $\Delta\phi_1, \Delta\phi_2, \Delta\phi_3$ to control the maneuvering apparatus 80. Here x, y, z defines the position of the center of gravity of the endoscopy capsule 10 in a Cartesian coordinate system, which can be predeteterminded for instance by the geometry of the maneuvering apparatus 80.

Second Exemplary Embodiment

Figure 2:
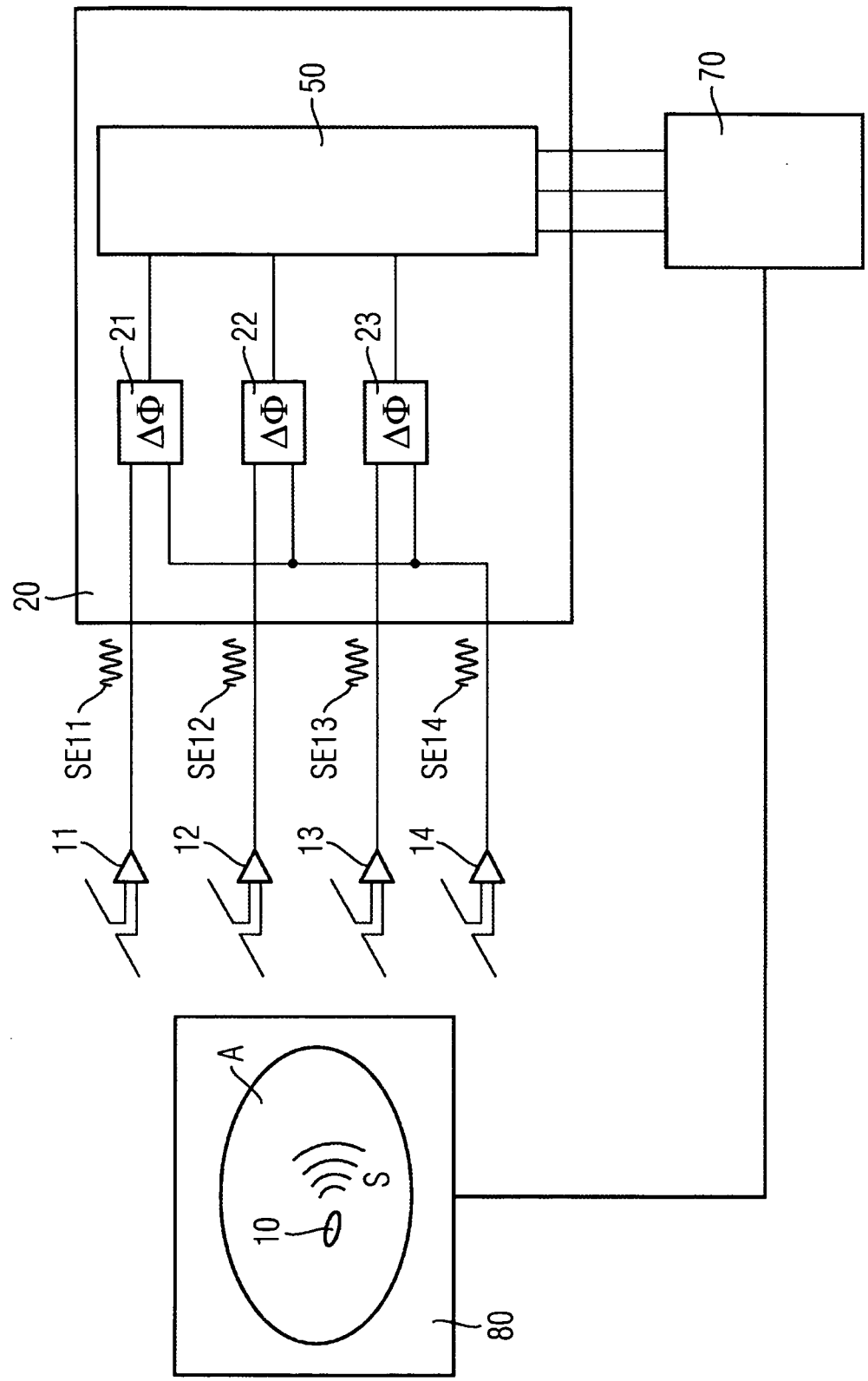
FIG. 2 shows a second exemplary embodiment of the proposed apparatus.

In a second, preferred exemplary embodiment, which is shown in FIG. 2, the medical device 10, as in the first exemplary embodiment, sends a modulated or non-modulated signal S with the aid of a transmit facility continuously or at intervals. The signal S is received by the receiving devices 11-14, with one of the receiving devices 11-14 subsequently being referred to as the first receive facility 14 and the remaining receiving devices being referred to as second receiving devices 11-13. The receiving devices 11-14 each include an antenna for receiving an electrical and/or a magnetic field and a preamplifier for amplifying the received signal.

The signals SE11-SE14 received and amplified with the receiving devices 11-14 are transmitted to a signal processing facility 20. In the signal processing facility 20, phase differences $\Delta\phi_1, \Delta\phi_2, \Delta\phi_3$ are determined between the signals SE11-SE13 received at the second receiving devices 11-13 and the signal SE14 received at the first receive facility 14, i.e. $\Delta\phi_1 = \phi(SE11) - \phi(SE14)$ $\Delta\phi_2 = \phi(SE12) - \phi(SE14)$, $\Delta\phi_3 = \phi(SE13) - \phi(SE14)$, with $\phi(X)$ symbolizing the phase of a signal X. The received signal SE14 of the first receive facility 14 is used correspondingly as a reference signal R within the meaning of the first exemplary embodiment.

Facilities 21-23, for instance phase detectors 21-23, are provided for determining the phase differences $\Delta\phi_1, \Delta\phi_2, \Delta\phi_3$, with the number of phase detectors 21-23 corresponding at least to the number of the second receiving devices 11-13.

Each phase detector 21-23 has a first and a second signal input and a signal output. In this way the first receive facility 14 for transmitting the received signal SE14 is connected to the first signal input of each phase detector 21-23. The second receiving devices 11-13 are each connected to the second signal input of the phase detectors 21-23, while the signal outputs for transmitting the determined phase differences $\Delta\phi_1$, $\Delta\phi_2$, $\Delta\phi_3$ are connected to a control facility 70.

Since the frequencies of the received signals SE11-SE14 are identical, it is possible to determine the phase differences in the second exemplary embodiment directly, contrary to the first exemplary embodiment.

The phase differences $\Delta\phi_1$, $\Delta\phi_2$, $\Delta\phi_3$ are fed to the control facility 70 as in the first exemplary embodiment. As in the first exemplary embodiment, the control facility 70 is connected to a maneuvering apparatus 80 for influencing the position x, y, z of the endoscopy capsule 10 and uses the phase differences $\Delta\phi_1$, $\Delta\phi_2$, $\Delta\phi_3$ to control the maneuvering apparatus 80.

The signal processing facility 20 is configured such that instead of the received signal SE14 of the first receive facility 14, a signal SE11-SE13 received at any of the other receiving devices 11-13 can be used as a reference signal R, i.e. for instance the signal SE12 of the receive facility 12. Accordingly, the phase differences $\Delta\phi_1$, $\Delta\phi_2$, $\Delta\phi_3$ would be calculated according to $\Delta\phi_1 = \phi(SE11) - \phi(SE12)$ $\Delta\phi_2 = \phi(SE13) - \phi(SE12)$, $\Delta\phi_3 = \phi(SE14) - \phi(SE12)$. The receive facility 12 then assumes the role of the first receive facility, while the receiving devices 11, 13, 14 form the group of the second receiving devices. A realization with the aid of a first and a second multiplexer would be conceivable, with the first multiplexer selecting one signal from the signals SE11-SE14, e.g. SE14 and outputting this to the first signal inputs of the phase detectors 21-23, while the second multiplexer selects the remaining three signals from the signals SE11-SE14, in the example SE11, SE12 and SE13 and forwards these to the second signal inputs in each case. Alternatively, other possibilities of defining any of the receiving devices 11-14 in a circuit-specific fashion as a first receive facility and conveying the signals SE11-SE14 accordingly to the first and second signal inputs of the phase detectors are also conceivable.

Figure 3:
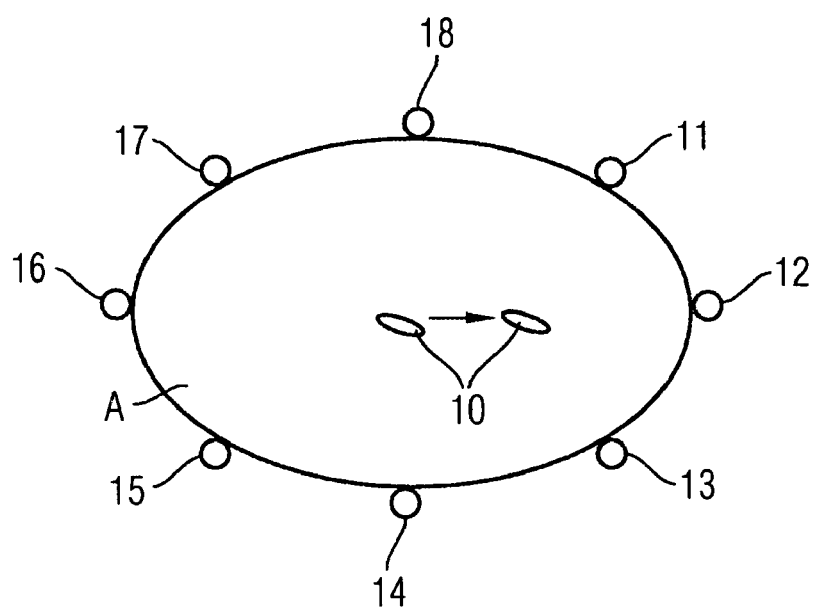
FIG. 3 shows an arrangement of a plurality of receiving devices and a medical device on a patient.

More than four receiving devices are advantageously used to increase the measuring accuracy. FIG. 3 shows a system comprising an endoscopy capsule 10 and eight receiving devices 11-18, which are attached in the region of a workspace A. In a concrete application, the workspace A can be the inside of a patient, with it being possible for the endoscopy capsule to be located in the stomach of the patient for instance. In addition to the receiving devices 11-18 shown in FIG. 3, further receiving devices can be provided in planes in front of and behind the image plane shown. The receiving devices are advantageously arranged such that the whole region to be examined with the endoscopy capsule 10 is surrounded by a network of receiving devices.

Functionality

The first and second exemplary embodiment differ in terms of providing the reference signal R. While a separate reference signal source 60 provides the reference signal R in the first exemplary embodiment, any of the receiving devices 11-14 in the second exemplary embodiment is used as a source of the reference signal R. The basic methods performed in the control facility 70 for controlling the position x,y,z of the endoscopy capsule 10 based on the determined phase differences $\Delta\phi_1$, $\Delta\phi_2$, $\Delta\phi_3$ are identical for both exemplary embodiments.

With the system shown in FIG. 3, seven phase differences $\Delta\phi_1$ to $\Delta\phi_7$ are determined and fed to the control facility 70. In the event that the endoscopy capsule 10 is not moved, i.e. is stationary relative to the receiving devices 11-18, the phase differences $\Delta\phi_1$ to $\Delta\phi_7$ are temporally constant.

If the capsule 10 is moved, at least some of the phase differences $\Delta\phi_1$ to $\Delta\phi_7$ change during the movement. It can generally be assumed here that a large change in a phase difference accompanies a large movement of the capsule 10 in the direction of the connecting line between the capsule 10 and that of the corresponding receive facility.

The control facility 70 evaluates the determined phase differences $\Delta\phi_1$ to $\Delta\phi_7$ by the temporal behavior $\Delta\phi_1(t)$ to $\Delta\phi_7(t)$ of the phase differences $\Delta\phi_1$ to $\Delta\phi_7$ fed thereto being monitored. The momentary, i.e. phase differences $\Delta\phi_1(t2)$ to $\Delta\phi_7(t2)$ determined at a time instant t2, are compared here with the phase differences $\Delta\phi_1(t1)$ to $\Delta\phi_7(t1)$ determined immediately beforehand at a time instant t1 (t1<t2).

Alternatively, the current phase differences $\Delta\phi_1(t1)$ to $\Delta\phi_7(t1)$ can be stored as reference values at a first arbitrary time instant t1. For instance, if an operator of the system has moved the endoscopy capsule 10 into a target position x(t1), y(t1), z(t1), in which a series of images of a certain region of the inside of the stomach is to be recorded, it is necessary for the capsule 10 to be stationary. At this time instant t1, the current phase differences $\Delta\phi_1(t1)$ to $\Delta\phi_7(t1)$ determined are stored by the operator pushing a button for instance. The subsequent phase differences $\Delta\phi_1(t)$ to $\Delta\phi_7(t)$ determined at second time instants t are continuously compared in the control facility 70 with the stored reference values $\Delta\phi_1(t1)$ to $\Delta\phi_7(t1)$.

With a change in one or several of the phase differences $\Delta\phi_1$ to $\Delta\phi$, a control of the maneuvering apparatus 80 is initiated by the control facility 70. In the two exemplary embodiments, the maneuvering apparatus 80 is preferably an arrangement with several individual coils for the contactless guidance of the endoscopy capsule 10, as is described for instance as a "magnetic coil arrangement" in DE 103 40 925 B3. The maneuvering apparatus 80 generates, by a correspondingly targeted current feed of the individual coils, one or several magnetic field components, $B_x$, $B_y$, $B_z$ and/or one or several gradient fields $G_{i,j} = \partial B_i/\partial j$ with i,j=x, y, z, as a result of which the interaction with the magnetic dipole moment of the permanent magnet of the capsule 10 can exert torques and/or forces on the capsule 10. The targeted current feed of the individual coils and consequently thereof the gradient fields $G_{i,j}$ and/or the magnetic field components $B_x$, $B_y$, $B_z$ are developed as a function of the control predetermined by the control facility 70.

The control takes place in this way in that with a change in the position x, y, z of the endoscopy capsule 10, which is connected to a change in one or several phase differences as described above, the gradient fields $G_{i,j}$ and/or the magnetic field components $B_x$, $B_y$, $B_z$ are adjusted so that the generated forces and torques counteract the detected movement of the capsule.

As the relationships between the current feed of one or several of the individual coils and the torques and forces thus generatable are known in respect of amount and direction, the movement of the endoscopy capsule which is detected by monitoring the phase differences can be selectively counteracted by the corresponding individual coils having current applied in accordance with the detected movement direction and if necessary amplitude. Reference is made to DE 103 40 925 B3 for the basic functionality of the maneuvering apparatus 80. The maneuvering apparatus 80 of the apparatus operates comparably, but is not defined in terms of design of the "magnetic coil arrangement" in DE 103 40 925 B3 but can instead also include more or fewer individual coils and be embodied in order to generate another number of magnetic degrees of freedom than the maneuvering apparatus or "magnetic coil arrangement" in DE 103 40 925 B3.

The result of the control of the maneuvering apparatus 80 by the control facility 70 is correspondingly such that the phase differences $\Delta\phi_1(t)$ to $\Delta\phi_7(t)$ remain temporally constant or the currently determined phase differences $\Delta\phi_1(t)$ to $\Delta\phi_7(t)$ correspond to the stored reference values $\Delta\phi_1(t1)$ to $\Delta\phi_7(t1)$.

Unwanted movements of the endoscopy capsule or deviations in the position x, y, z of the capsule 10 from a target position x(t1), y(t1), z (t1) can be counteracted.

Further Embodiments

Figure 4:
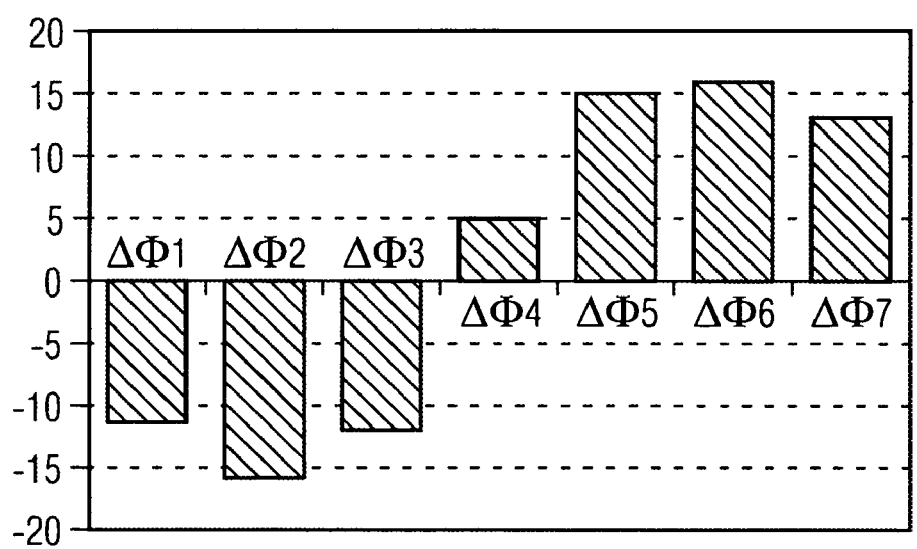
FIG. 4 shows an overview of the changes in phase difference occurring during a movement of a medical device according to FIG. 3

The movement of the capsule 10 in the x-direction, which is indicated by the arrow in FIG. 3, is reflected in a comparatively large change in the phase differences $\Delta\phi_2$, $\Delta\phi_6$ determined in respect of the receiving devices 12, 16. The phase differences $\Delta\phi_4$, $\Delta\phi_6$ determined in respect of the receiving devices 14, 18 are by contrast not changed or only changed minimally. FIG. 4 shows a diagram, in which, for the receiving devices 11-18, the changes in the phase differences $\Delta\phi_1$, $\Delta\phi_7$, are plotted in any units, which can result during a movement of the capsule 10 in the x-direction according to FIG. 3.

During the evaluation of the phase differences in the control facility 70, only a limited number of phase differences, in particular only the largest phase differences $\Delta\phi_1$, $\Delta\phi_2$, $\Delta\phi_3$, $\Delta\phi_5$, $\Delta\phi_6$, $\Delta\phi_7$ are preferably taken into account, while the remaining $\Delta\phi_4$ is disregarded. A weighting can alternatively take place in accordance with the sums of the phase differences.

In the event that the endoscopy capsule is equipped with an imaging system such as a camera and transmits a video signal, the transmitter available for this purpose in the capsule can also be used to transmit the signal S, with a carrier frequency of 433 MHz typically being used. It is then possible to dispense with a separate transmit facility or other additional equipment in the capsule for transmitting the signal S for position control purposes. The transmit program of the capsule must possibly be changed such that the image transmission is interrupted at predetermined intervals and a non-modulated signal is sent for the position measurement for a few microsecs.

The receiving devices can be attached directly to the patient, for instance by adhesion to the skin, or on the maneuvering apparatus 80. For practical reasons, the receiving devices inside the cylindrical maneuvering apparatus 80 are attached to the inner cylinder wall in the case of a maneuvering apparatus 80 and/or magnetic coil arrangement as described in DE 103 40 925 B3 for instance.

The invention has been described in detail with particular reference to preferred embodiments thereof and examples, but it will be understood that variations and modifications can be effected within the spirit and scope of the invention covered by the claims which may include the phrase "at least one of A, B and C" as an alternative expression that means one or more of A, B and C may be used, contrary to the holding in Superguide v. DIRECTV, 69 USPQ2d 1865 (Fed. Cir. 2004).

The invention claimed is:

1. A method for controlling a position of a medical device in a workspace, comprising:
sending a signal from a transmitter in the medical device, to a plurality of receiving devices;
determining respective phase differences in a signal processing unit, between a reference signal and signals received at the receiving devices from the transmitter;
feeding the phase differences to a control unit; and
controlling a maneuvering apparatus for influencing the position of the medical device as a function of the phase differences, the maneuvering apparatus being controlled at the control unit,
wherein the reference signal is generated by a reference signal source separate from the transmitter in the medical device and the receiving devices.

2. The method as claimed in claim 1, wherein
phase deviations between the reference signal and the signals received at the receiving devices are determined in the signal processing unit, and
the phase differences are determined from the phase deviations.

3. The method as claimed in claim 2, wherein in order to determine the phase differences
one of the phase deviations is used as a reference value, and
a difference is calculated between the remaining phase deviations and the reference value.

4. The method as claimed in claim 1, wherein the control unit controls the maneuvering apparatus such that the phase differences remain temporally constant.

5. The method as claimed in claim 4, wherein the maneuvering apparatus generates at least one gradient field and/or at least one magnetic field component under the control of the control unit.

6. The method as claimed in claim 4, wherein the maneuvering apparatus is controlled such that it generates forces on the medical device, which counteract a movement of the medical device or a deviation of the position of the medical device from a target position.

7. The method as claimed in claim 1, wherein phase differences determined at a time instant are stored as stored phase differences.

8. The method as claimed in claim 7, wherein the control unit controls the maneuvering apparatus such that the phase differences correspond to the stored phase differences.

9. The method as claimed in claim 1, wherein less than all of phase differences is taken into consideration for controlling the maneuvering apparatus.

10. The method as claimed in claim 1, wherein only a largest phase difference is taken into consideration for controlling the maneuvering apparatus.

11. An apparatus for controlling a position of a medical device in a workspace, the medical device including a transmitter for transmitting a signal, the apparatus comprising:
a plurality of receiving devices to receive the signal;
a reference signal source to generate a reference signal, the reference signal source being generated separate from the transmitter in the medical device and the receiving devices;
a signal processing unit to determine respective phase differences between the signals received at the receiving devices and the reference signal, with the receiving devices and the reference signal source being connected to different inputs of the signal processing unit; and
a position control unit connected to the signal processing unit.

12. The apparatus as claimed in claim 11, wherein the signal processing unit comprises:
a phase deviation unit to determine respective phase deviations between the reference signal and the signals received at the receiving devices; and
a difference formation apparatus to determine the phase differences from the phase deviations.

13. The apparatus as claimed in claim 12, wherein
there are a plurality of phase deviation units,
each phase deviation unit has a first and a second signal input and a signal output,
the reference signal source is connected to the first signal input of each phase deviation unit,
the receiving devices are respectively connected to the second signal input of phase deviation units,
the signal outputs of the phase deviation units are connected to the difference formation apparatus, and the difference formation apparatus is connected to the control unit for transmitting the phase differences.

14. The apparatus as claimed in claim 12, wherein the number of phase deviation units corresponds to the number of receiving devices.

15. The apparatus as claimed in claim 13, wherein
the phase deviation units each include a mixing device and a phase measurer,
the mixing device has an output,
the phase measurer has an output,
the first and the second signal input are connected to the mixing device,
the phase measurer is connected to the output of the mixing device, and
the output of the phase measurer is connected to the difference formation apparatus.

16. The apparatus as claimed in claim 11, wherein
the control unit is connected to a maneuvering apparatus to influence the position of the medical device,
the maneuvering apparatus is a coil arrangement for the contact-free guidance of the medical device, and
the medical device is an endoscopy capsule.

17. The apparatus as claimed in claim 11, wherein the medical device comprises a magnetic and a contact-free navigable endoscopy capsule.

18. An apparatus for controlling a position of a medical device in a workspace, the medical device including a transmitter to transmit a signal, the apparatus comprising:
a plurality of receiving devices to receive the signal, the receiving devices comprising a first receiving device and two or more second receiving devices,
wherein the signal received by the first receiving device is determined as a reference signal;
a signal processing unit to determine respective phase differences between each of the signals received at the second receiving devices and the reference signal of the first receiving device, with the plurality of receiving devices being connected to the signal processing unit for transmission of the signals; and
a position control unit connected to the signal processing unit to receive the phase differences.

19. The apparatus as claimed in claim 18, wherein
the signal processing unit contains a plurality of phase detectors to determine the phase differences, and
the number of phase detectors is equal to the number of second receiving devices.

20. The apparatus as claimed in claim 19, wherein
each phase detector comprises a first and a second signal input and a signal output,
the first receiving device is connected to the first signal input of each phase detector such that each phase detector is provided with the signal from the first receiving device,
the second receiving devices are connected respectively to the second signal input of the phase detectors, and
the signal outputs of the phase detectors are connected to the control unit such that the control unit receives the phase differences.

21. A method for controlling a position of a medical device in a human body, comprising:
sending a signal from a transmitter in the medical device, to a plurality of receiving devices, the plurality of receiving devices including a first receiving device and a plurality of second receiving devices,
wherein the signal received by the first receiving device is determined as a reference signal;
determining respective phase differences between the reference signal of the first receiving device and each of the signals received at the second receiving devices from the transmitter;
determining a position change of the medical device based on the phase differences, without determining an absolute position of the medical device; and
using an external control unit to control a maneuvering apparatus in the medical device as a function of the phase differences, the maneuvering apparatus being controlled to counteract the position change and maintain a substantially uniform placement of the medical device in the human body.

22. The method as claimed in claim 21, wherein a plurality of phase detectors are used to determine the phase differences, and the number of phase detectors is less than the total number of receiving devices.

* * * * *